(12) United States Patent
Xu et al.

(10) Patent No.: US 10,888,622 B2
(45) Date of Patent: Jan. 12, 2021

(54) NANOCOMPLEXES OF MODIFIED PEPTIDES OR PROTEINS

(71) Applicant: Trustees of Tufts College, Medford, MA (US)

(72) Inventors: Qiaobing Xu, Lexington, MA (US); Ming Wang, Beijing (CN)

(73) Assignee: Trustees of Tufts College, Medford, MA (US)

(*) Notice: Subject to any disclaimer, the term of this patent is extended or adjusted under 35 U.S.C. 154(b) by 0 days.

(21) Appl. No.: 14/890,441

(22) PCT Filed: May 13, 2014

(86) PCT No.: PCT/US2014/037816
§ 371 (c)(1),
(2) Date: Nov. 11, 2015

(87) PCT Pub. No.: WO2014/186348
PCT Pub. Date: Nov. 20, 2014

(65) Prior Publication Data
US 2016/0129120 A1    May 12, 2016

Related U.S. Application Data

(60) Provisional application No. 61/823,098, filed on May 14, 2013.

(51) Int. Cl.
| A61K 38/00 | (2006.01) |
| A61K 47/54 | (2017.01) |
| A61K 9/16 | (2006.01) |
| A61K 38/46 | (2006.01) |

(52) U.S. Cl.
CPC .............. *A61K 47/542* (2017.08); *A61K 9/16* (2013.01); *A61K 38/465* (2013.01); *A61K 47/54* (2017.08); *A61K 47/541* (2017.08); *C12Y 301/27005* (2013.01)

(58) Field of Classification Search
None
See application file for complete search history.

(56) References Cited

U.S. PATENT DOCUMENTS

2005/0025821 A1* 2/2005 Harvie ................. A61K 9/1272
424/450
2008/0280856 A1* 11/2008 Cohen ..................... C07F 5/025
514/64

2011/0293703 A1   12/2011  Mahon et al.
2011/0312905 A1   12/2011  Cohen et al.
2012/0009222 A1    1/2012  Nguyen et al.

OTHER PUBLICATIONS

Dalkara, D., et al. Molecular Therapy (2004), 9(6); pp. 964-969.*
Pierce product bulletin for NHS—Fluorescein; Oct. 2005.*
Yu, M., et al. Nano Lett. (2008), 8(10); pp. 3510-3515 (Year: 2008).*
Akinc, et al., "A combinatorial library of lipid-like materials for delivery of RNAi therapeutics", Nature Biotechnology, 2008, vol. 25, No. 5, pp. 561-569.
Jourden, et al., "Hydrogen peroxide activated matrix metalloproteinase inhibitors: A prodrug approach", Angewandte Chemie International Edition, 2010, vol. 49, pp. 6795-5797.
Jourden, et al., "Investigation of self-Immolative linkers in the design of hydrogen peroxide activated metalloprotein inhibitors", Chemistry Communication, 2011, vol. 47, pp. 7968-7970.
Broaders, et al., "A biocompatible oxidation-triggered carrier polymer with potential in therapeutics", Journal of the American Chemical Society, 2011, vol. 133, pp. 756-758.
Kuang, et al., "Hydrogen peroxide inducible DNA cross-linking agents: Targeted anticancer prodrugs", Journal of the American Chemical Society, 2011, vol. 133, pp. 19278-19281.
Wang, et al., "Combinatorial library of unsaturated lipidoids for efficient intracellular gene delivery", ACS Synthetic Biology, 2012, vol. 1, No. 9, pp. 403-407.
Sun, et al., "Combinatorial library of lipidoids for in vitro DNA delivery", Bioconjugate Chemistry, 2012, vol. 23, No. 1, pp. 135-140.
Lux, et al., "Biocompatible polymeric nanoparticles degrade and release cargo in response to biologically relevant levels of hydrogen peroxide", Journal of the American Chemical Society, 2012, vol. 134, pp. 15758-15764.

* cited by examiner

*Primary Examiner* — Kevin S Orwig
(74) *Attorney, Agent, or Firm* — Dana M. Gordon; Foley Hoag LLP

(57) ABSTRACT

A nanocomplex containing a delivery agent and a pharmaceutical agent. The nanocomplex has a particle size of 50 to 1000 nm, the delivery agent binds to the pharmaceutical agent via non-covalent interaction or covalent bonding, and the pharmaceutical agent is a modified peptide or protein formed of a peptide or protein and an added chemical moiety that contains an anionic group, a disulfide group, a hydrophobic group, a pH responsive group, a light responsive group, a reactive oxygen species responsive group, or a combination thereof.

5 Claims, No Drawings

NANOCOMPLEXES OF MODIFIED PEPTIDES OR PROTEINS

CROSS REFERENCE TO RELATED APPLICATIONS

This application is the National Stage of International Application No. PCT/US2014/037816, filed on May 13, 2014, which claims the benefit of U.S. Provisional Application No. 61/823,098, filed on May 14, 2013. The contents of both applications are hereby incorporated by reference in their entirety.

BACKGROUND

Delivery of protein to cells is challenging, given the low permeability and stability of most proteins. Indeed, it is the major hurdle in protein therapy.

Hypodermic injection still remains the most widely used route for protein delivery, even though it is inconvenient and expensive.

Delivery agents have been developed for transporting protein into cells. However, proteins delivered by these agents typically exhibit low bioavailability, as they often are not easily released into the cells effectively, see Brown, Expert Opinion on Drug Delivery, 2, 29-42 (2005).

There is a need to develop a system efficient in delivering proteins into cells.

SUMMARY

This invention is based on the discovery that certain nanocomplexes can be used to efficiently deliver peptides or proteins into cells.

Each of these nanocomplexes is formed of a delivery agent and a pharmaceutical agent. It has a particle size of 50 to 1000 nm. The delivery agent binds to the pharmaceutical agent via non-covalent interaction or covalent bonding and the pharmaceutical agent is a modified peptide or protein formed of a peptide or protein and an added chemical moiety that contains an anionic group, a disulfide group, a hydrophobic group, a pH responsive group, a light responsive group, a reactive oxygen species responsive group, or a combination thereof.

In one embodiment, the pharmaceutical agent is cationic that is capable of being positively charged and the pharmaceutical agent is a modified peptide or protein including an added chemical moiety that contains an anionic group, i.e., an anion or a group that can be negatively charged.

The delivery agent, which can be a compound or particle that is positively charged or can be positively charged, is typically a surfactant, a lipid, a lipid-like compound, a polymer, a dendrimer, an inorganic nanoparticle, a polymer nanoparticle, an inorganic nanowire, a polymer nanowire, a nanotube, or a combination thereof. Preferably, the delivery agent is a bio-reducible material, e.g., a bio-reducible polymer and a bio-reducible lipid-like compound.

As an example, a lipid-like compound has the following formula:

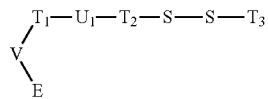

in which (i) V is a hydrophilic head, (ii) E is a $C_1$-$C_{24}$ monovalent aliphatic radical, a $C_1$-$C_{24}$ monovalent heteroaliphatic radical, a monovalent aryl radical, a monovalent heteroaryl radical, or $T_4$-$U_2$-$T_5$-S—S-$T_6$, (iii) $T_2$-S—S-$T_3$ is a hydrophobic tail, and (iv) $U_1$ and $U_2$ are each a linker (see discussion below). Each of $T_1$ and $T_4$, independently, is a bond, a $C_1$-$C_{10}$ bivalent aliphatic radical, a $C_1$-$C_{10}$ bivalent heteroaliphatic radical, a bivalent aryl radical, or a bivalent heteroaryl radical; each of $T_2$ and $T_5$, independently, is a bond, a $C_1$-$C_{20}$ bivalent aliphatic radical, a $C_1$-$C_{20}$ bivalent heteroaliphatic radical, a bivalent aryl radical, or a bivalent heteroaryl radical; and each of $T_3$ and $T_6$, independently, is a $C_1$-$C_{20}$ monovalent aliphatic radical, a $C_1$-$C_{20}$ monovalent heteroaliphatic radical, a monovalent aryl radical, or a monovalent heteroaryl radical. S—S stands for a disulfide moiety.

The hydrophilic head contains one or more hydrophilic functional groups, e.g., hydroxyl, carbonyl, carboxyl, amino, sulfhydryl, phosphate, amide, ester, ether, carbamate, carbonate, carbamide, and phosphodiester. These groups can form hydrogen bonds and are optionally positively or negatively charged.

The hydrophobic tail is a saturated or unsaturated, linear or branched, acyclic or cyclic, aromatic or nonaromatic hydrocarbon moiety containing a disulfide bond and 8-24 carbon atoms. One or more of the carbon atoms can be replaced with a heteroatom, such as N, O, P, B, S, Si, Sb, Al, Sn, As, Se, and Ge. The lipid-like compounds containing this disulfide bond can be bioreducible.

Turning to the linker(s), it links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate, phosphate, phosphite, sulfate, sulfite, and thiosulfate.

The lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

The modified peptide or protein is formed of a peptide or protein and an added chemical moiety. Typically, the added chemical moiety is linked to the peptide or protein via a linking group, e.g., an amide group, an ester group, an ether group, a thioether group, a disulfide group, a hydrazone group, a sulfenate ester group, an amidine group, a urea group, a carbamate group, an imidoester group, and a carbonate group. Preferably, the linking group is an amide group, an ester group, a disulfide group, a thioester group, or a carbamate group.

The added chemical moiety may contain a $C_1$-$C_{10}$ heteroaliphatic radical, an aryl radical, or a heteroaryl radical. Examples include

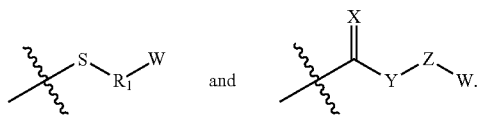

In these two formulae, $R_1$, W, X, Y, and Z represent the groups described below.

(i) $R_1$ is a bond, a $C_1$-$C_{10}$ bivalent aliphatic radical, a $C_1$-$C_{10}$ bivalent heteroaliphatic radical, a bivalent aryl radical, or a bivalent heteroaryl radical.

(ii) W is a boronic ester group or an anionic group. The latter can be

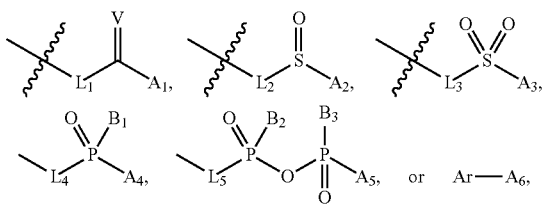

in which each of $A_1$, $A_2$, $A_3$, $A_4$, $A_5$, and $A_6$, independently, is $O^-$ or $S^-$; Ar is aryl or heteroaryl; each of $B_1$, $B_2$, and $B_3$, independently, is $O^-$, $OR_a$, $S^-$, or $SR_b$; each of $L_1$, $L_2$, $L_3$, $L_4$, and $L_5$, independently, is a bond, O, S, or $NR_c$; and V is O, S, or $NR_d$, wherein each of $R_a$, $R_b$, $R_c$, and $R_d$, independently, is, H, OH, an amino acid radical, a peptide radical, a $C_1$-$C_{10}$ monovalent aliphatic radical, a $C_1$-$C_{10}$ monovalent heteroaliphatic radical, a monovalent aryl radical, or a monovalent heteroaryl radical.

Examples include $-CO_2^-$, $-CO_2H$, $-SO_3^-$, $-SO_3H$, $-SO_2^-$, $-ArO^-$, $-ArS^-$, $-PO_3^{2-}$, $-PO_3H^-$, $-P(O)(OR_a)O^-$, $-PO_4^{2-}$, $-OP(O)(OH)O^-$, $-OP(O)(OH)OP(O)(OH)O^-$, $-OP(O)(OH)OP(O)O_2^{2-}$, and $-OP(O)(O^-)OP(O)O_2^{2-}$. Preferably, the anionic group is $-CO_2^-$ or $-SO_3^-$.

(iii) X is O, S, or $NR_e$, in which $R_e$ is H, OH, an amino acid radical, a peptide radical, a $C_1$-$C_{10}$ monovalent aliphatic radical, a $C_1$-$C_{10}$ monovalent heteroaliphatic radical, a monovalent aryl radical, or a monovalent heteroaryl radical.

(iv) Y is a bond, O, S, or $NR_f$, in which $R_f$ is H, OH, an amino acid radical, a peptide radical, a $C_1$-$C_{10}$ monovalent aliphatic radical, a $C_1$-$C_{10}$ monovalent heteroaliphatic radical, a monovalent aryl radical, or a monovalent heteroaryl radical.

(v) Z is a bond, $R_g$, or $R_h$-$A_7$-$A_8$-$R_i$, in which each of $R_g$, $R_h$, and $R_i$, independently, is a bond, an amino acid radical, a peptide radical, a $C_1$-$C_{10}$ bivalent aliphatic radical, a $C_1$-$C_{10}$ bivalent heteroaliphatic radical, a bivalent aryl radical, or a bivalent heteroaryl radical; $A_7$ is a bivalent aryl radical or a bivalent heteroaryl radical; and $A_8$ is a bond, O, S, or NR', wherein R' is H, OH, an amino acid radical, a peptide radical, a $C_1$-$C_{10}$ monovalent aliphatic radical, a $C_1$-$C_{10}$ monovalent heteroaliphatic radical, a monovalent aryl radical, or a monovalent heteroaryl radical.

Five specific added chemical moieties are shown below:

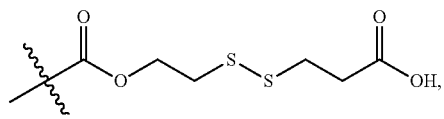

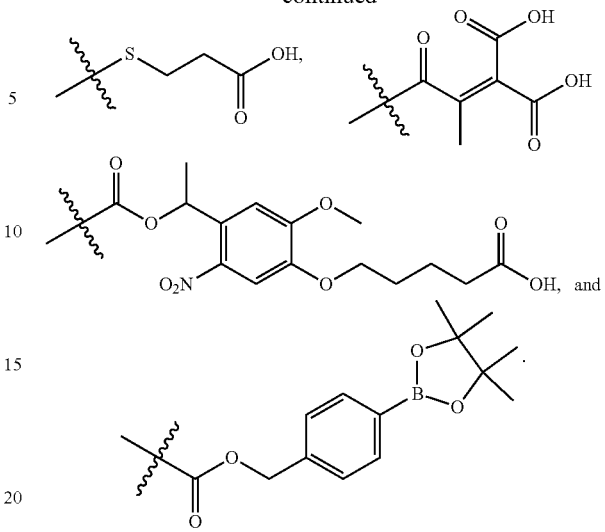

The term "non-covalent interaction" refers to any non-covalent binding, which includes ionic interaction, hydrogen bonding, van der Waals interaction, and hydrophobic interaction.

The term "peptide" or "protein" refers to a polymer of natural or non-natural amino acids linked together by amide bonds. In general, a peptide contains 2-50 amino acid residues. There are more amino acid residues in a protein.

The term "aliphatic" herein refers to a saturated or unsaturated, linear or branched, acyclic, cyclic, or polycyclic hydrocarbon moiety. Examples include alkyl, alkylene, alkenyl, alkenylene, alkynyl, alkynylene, cycloalkyl, cycloalkylene, cycloalkenyl, cycloalkenylene, cycloalkynyl, and cycloalkynylene moieties. The term "alkyl" or "alkylene" refers to a saturated, linear or branched hydrocarbon moiety, such as methyl, methylene, ethyl, ethylene, propyl, propylene, butyl, butylenes, pentyl, pentylene, hexyl, hexylene, heptyl, heptylene, octyl, octylene, nonyl, nonylene, decyl, decylene, undecyl, undecylene, dodecyl, dodecylene, tridecyl, tridecylene, tetradecyl, tetradecylene, pentadecyl, pentadecylene, hexadecyl, hexadecylene, heptadecyl, heptadecylene, octadecyl, octadecylene, nonadecyl, nonadecylene, icosyl, icosylene, triacontyl, and triacotylene. The term "alkenyl" or "alkenylene" refers to a linear or branched hydrocarbon moiety that contains at least one double bond, such as $-CH=CH-CH_3$ and $-CH=CH-CH_2-$. The term "alkynyl" or "alkynylene" refers to a linear or branched hydrocarbon moiety that contains at least one triple bond, such as $-C\equiv C-CH_3$ and $-C\equiv C-CH_2-$. The term "cycloalkyl" or "cycloalkylene" refers to a saturated, cyclic hydrocarbon moiety, such as cyclohexyl and cyclohexylene. The term "cycloalkenyl" or "cycloalkenylene" refers to a non-aromatic, cyclic hydrocarbon moiety that contains at least one double bond, such as cyclohexenyl cyclohexenylene. The term "cycloalkynyl" or "cycloalkynylene" refers to a non-aromatic, cyclic hydrocarbon moiety that contains at least one triple bond, cyclooctynyl and cyclooctynylene.

The term "heteroaliphatic" herein refers to an aliphatic moiety containing at least one heteroatom selected from N, O, P, B, S, Si, Sb, Al, Sn, As, Se, and Ge.

The term "aryl" herein refers to a $C_6$ monocyclic, $C_{10}$ bicyclic, $C_{14}$ tricyclic, $C_{20}$ tetracyclic, or $C_{24}$ pentacyclic aromatic ring system. Examples include phenyl, phenylene, naphthyl, naphthylene, anthracenyl, anthrcenylene, pyrenyl, and pyrenylene.

The term "heteroaryl" herein refers to an aromatic 5-8 membered monocyclic, 8-12 membered bicyclic, 11-14 membered tricyclic, and 15-20 membered tetracyclic ring system having one or more heteroatoms (such as O, N, S, or Se). Examples include furyl, furylene, fluorenyl, fluorenylene, pyrrolyl, pyrrolylene, thienyl, thienylene, oxazolyl, oxazolylene, imidazolyl, imidazolylene, benzimidazolyl, benzimidazolylene, thiazolyl, thiazolylene, pyridyl, pyridylene, pyrimidinyl, pyrimidinylene, quinazolinyl, quinazolinylene, quinolinyl, quinolinylene, isoquinolyl, isoquinolylene, indolyl, and indolylene.

Unless specified otherwise, aliphatic, heteroaliphatic, oxyaliphatic, alkyl, alkylene, alkenyl, alkenylene, alkynyl, alkynylene, cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl mentioned herein include both substituted and unsubstituted moieties. Possible substituents on cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl include $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_3$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_2$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on aliphatic, heteroaliphatic, oxyaliphatic, alkyl, alkylene, alkenyl, alkenylene, alkynyl, and alkynylene include all of the above-recited substituents except $C_1$-$C_{10}$ alkyl. Cycloalkyl, cycloalkylene, cycloalkenyl, cycloalkenylene, heterocycloalkyl, heterocycloalkylene, heterocycloalkenyl, heterocycloalkenylene, aryl, and heteroaryl can also be fused with each other.

The cationic delivery agent and the anionic pharmaceutical agent described above include the compounds themselves, as well as their salts and solvates, if applicable. A salt, for example, can be formed between an anion and a positively charged group (e.g., amino) on these compounds. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on these compounds. Suitable cations include sodium ion, potassium ion, magnesium ion, calcium ion, and an ammonium cation such as tetramethylammonium ion. The compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

The details of one or more embodiments of the invention are set forth in the description and the drawing below. Other features, objects, and advantages of the invention will be apparent from the description, the drawing, and the claims.

DETAILED DESCRIPTION

The nanocomplex of this invention contains a modified peptide or protein. The modification can be achieved by attaching to a peptide or protein, non-covalently or covalently, a chemical moiety that contains an anionic group, a disulfide group, a hydrophobic group, a pH responsive group, a light responsive group, a reactive oxygen species responsive group, or a combination thereof.

Non-covalent bonding refers to ionic interaction, hydrogen bonding, van der Waals interaction, and hydrophobic interaction. On the other hand, covalent bonding is typical formed by crosslinking a chemical moiety to a functional group (e.g., —$NH_2$, —NH—, —COOH, —SH, —C(O)—, and —CHO) on a peptide or protein.

Crosslinking agents are generally used to modify a peptide or protein. Examples include anhydrides, carbonates, sulfonothinates, carbodiimides, disuccinimidyl suberate, symmetric disulfides, sulfosuccinimidyl-4-(N-maleimidomethyl)cyclohexane-1-carboxylate, N-hydroxysuccinimide esters, imidoesters, maleimides, haloacetyls, alkyl halides, pyridyl disulfides, hydrazides, alkoxyamines, aryl azides, and diazirines. The exemplary crosslinking agents are described in detail below.

An anhydride reacts with a —$NH_2$ or —NH— group on a peptide or protein. Cyclic anhydrides and anionic group-containing anhydrides are particularly useful. Examples include cis-aconitic anhydride, 4-methyl-2,5-dioxo-2,5-dihydrofuran-3-carboxylic acid, 2,6-dioxo-5,6-dihydro-2H-pyran-3-carboxylic acid, and 4-methyl-2,6-dioxo-5,6-dihydro-2H-pyran-3-carboxylic acid.

A carbonate also reacts with —$NH_2$/—NH— to form a carbamate group. Examples include

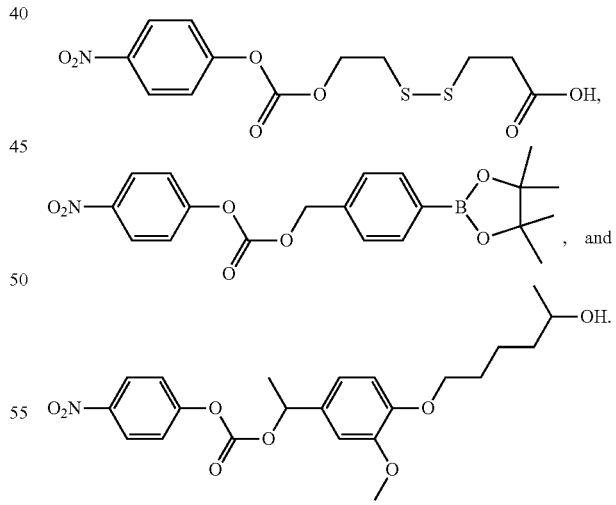

A sulfonothinate (e.g., 3-(methylsulfonylthio)propanoic acid) reacts with the —SH group on a cysteine residue in a peptide or protein, forming a disulfide bond.

A carbodiimide, e.g., N,N'-dicyclohexylcarbodiimide and 1-ethyl-3-(3-dimethylaminopropyl)carbodiimide), activates a carboxyl group or a phosphate group to couple it with —$NH_2$/—NH— to yield an amide bond.

Disuccinimidyl suberate has the following formula:

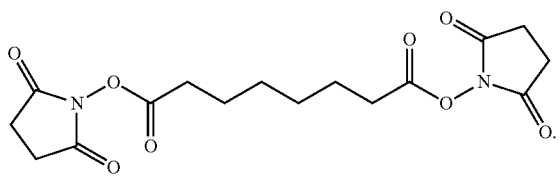 [SMILES: O=C(CCCCCCC(=O)ON1C(=O)CCC1=O)ON1C(=O)CCC1=O]

It reacts with —NH$_2$/—NH— to form an amide group.

A symmetric disulfide has the following formula: R—S—S—R, in which R contains an anionic group. It reacts with —SH to form a mixed disulfide group. Examples include 5,5'-dithio-bis-(2-nitrobenzoic acid) and N,N'-didansyl-L-cystine.

Sulfosuccinimidyl-4-(N-maleimidomethyl)cyclohexane-1-carboxylate has the following formula:

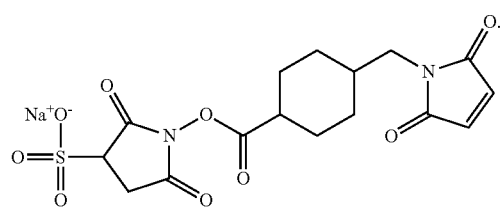

It can react with —NH$_2$/—NH— to form an amide group and can also react with —SH to form a thioether group.

An N-hydroxysuccinimide ester has the following formula:

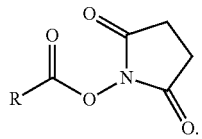

It reacts with —NH$_2$/—NH— to form an amide group.

An imidoester has the following formula:

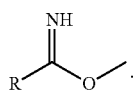

It reacts with —NH$_2$/—NH— to form an amidine group.

A maleimide has the following formula:

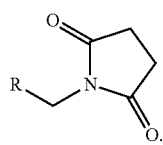

It reacts with —SH to form a thioether group.

A haloacetyl has the following formula:

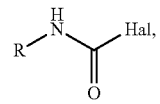

in which Hal is I or Br. It can react with —NH$_2$/—NH— to form an amine group and can also react with —SH to form a thioether group.

An alkyl halide has the following formula: RCH$_2$—Hal. It can react with —NH$_2$/—NH— to form an amine group and can also react with —SH to form a thioether group.

A pyridyl disulfide has the following formula:

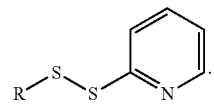

It reacts with —SH to form a disulfide group.

A hydrazide has the following formula:

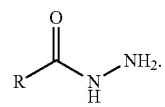

It reacts with a carbonyl group (aldehyde and ketone) in a peptide or protein to form a hydrazone group.

An alkoxyamine has the following formula:

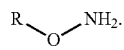

It reacts with a carbonyl group to form an imidoester group.

An aryl azide has the following formula:

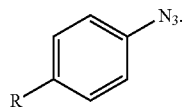

Upon being exposed to UV light, the aryl group insert into C—H or N—H on a peptide or protein.

A diazirine has the following formula:

Like an aryl azide, it insert into C—H or N—H upon being exposed to UV light.

A peptide or protein can react with 4-chloro-7-nitro-1,2,3-benzoxadiazole to form a amine or thioether group and can also react with methyl methanethiosulfonate to form —S—S—CH$_3$.

In addition, a peptide or protein can be modified through a traceless Staudinger ligation. See Bernardes et al., ChemBioChem, 12, 1383-86 (2011); Tam et al., Methods Enzymol., 462, 25-44 (2009); and Hayashi et al., Accounts of Chemical Research, 45, 1460-69 (2012).

More examples of peptide/protein modification are described in Lee et al., Angewandte Chemie International Edition, 48, 5309-12 (2009); Lee et al., Angewandte Chemie International Edition, 49, 2552-55 (2010); and Maier et al., Journal of American Chemical Society, 134, 10169-73 (2012).

Preferably, the peptide/protein modification is reversible. Namely, after the modified peptide/protein, as a component of a nanocomplex, enters a cell, the added chemical moiety can be cleaved by a redox enzyme or light, or as a result of pH change.

For example, a protein containing a lysine residue is modified with a disulfide moiety. After the modified protein enters a cell, the disulfide moiety is removed by glutathione (hereinafter "GSH") or other cysteine residues to regenerate the nascent protein. See Scheme 1 below.

Scheme 1. Protein modified on a lysine residue with a disulfide moiety

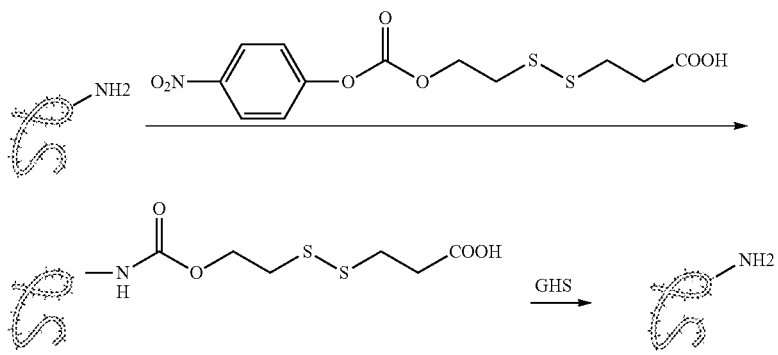

As another example, a protein containing a cysteine residue is modified with a negatively charged disulfide moiety. After the modified protein enters a cell, the moiety is then reduced by GSH, as shown in Scheme 2 below:

Scheme 2. Protein modified on a cysteine residue with a disulfide moiety

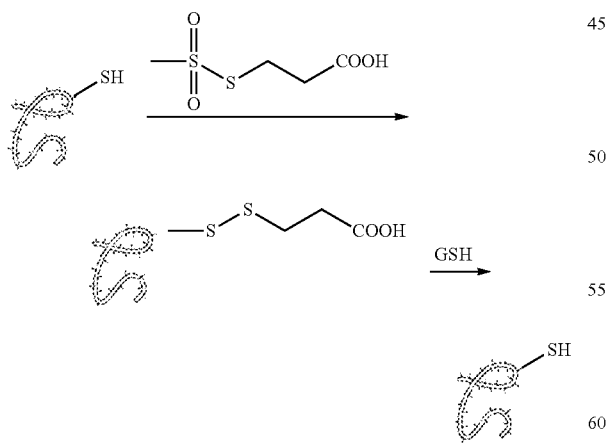

As a further example, a protein is modified with a light responsive moiety. After being delivered to a cell, the modified protein is exposed to light to remove the moiety. See Scheme 3 below.

Scheme 3. Protein modified with a light responsive moiety

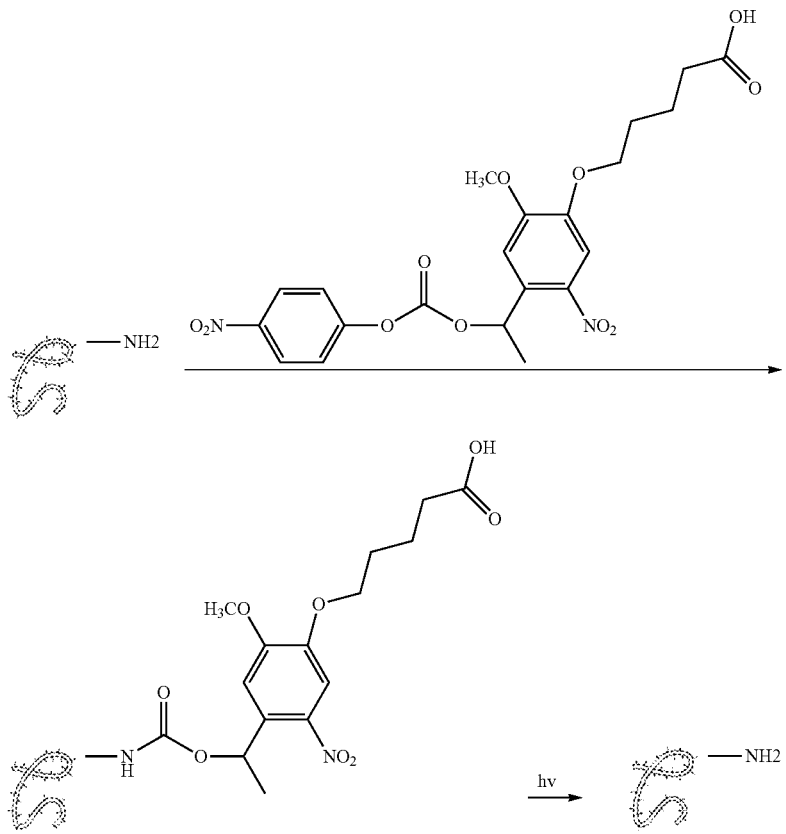

As still another example, a protein is modified with a pH responsive moiety. After the modified protein enters a cell, the moiety is cleaved in, e.g., an endosome of the cell. See Scheme 4 below.

Scheme 4. Protein modified with a pH responsive moiety

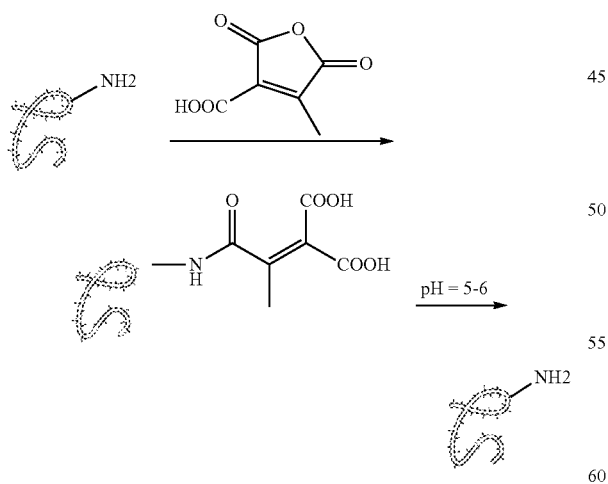

As yet another example, a protein is modified with a reactive oxygen species (ROS) responsive moiety, shown in Scheme 5 below as BNC. After the modified protein enters a cell, the moiety is cleaved by ROS, e.g., $H_2O_2$. See Scheme 5.

Scheme 5. Protein modified with a ROS responsive moiety

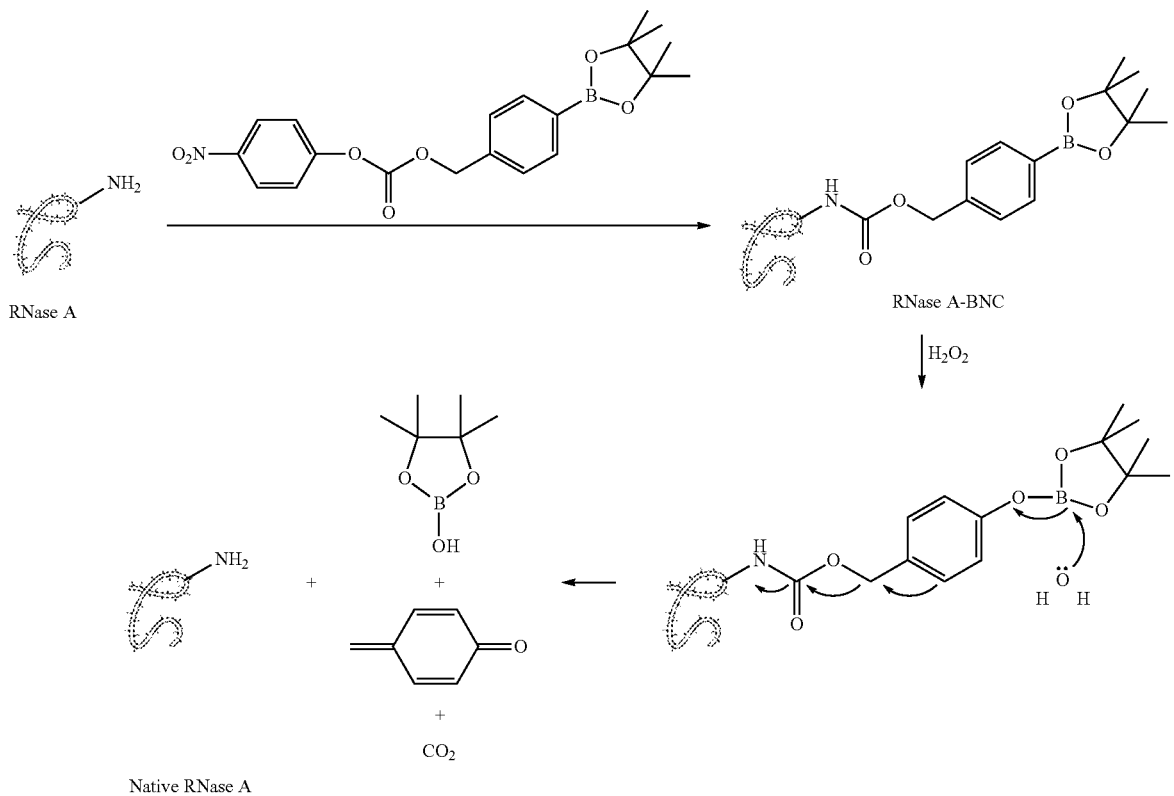

The peptide/protein thus modified has an isoelectric point of 9.6 to 3.6 (e.g., 8.5 to 4.8 and 6.5 to 5.5). Nanocomplexes containing the modified peptide/protein described above are useful for delivering a peptide or protein into a cell. These nanocomplexes can be preliminarily screened for their delivery efficacy by an in vitro assay and then confirmed by animal studies and clinic trials. Other methods will also be apparent to those of ordinary skill in the art.

The above-described nanocomplexes can be prepared using the procedures described in publications such as Wang et al., ACS Synthetic Biology, 1, 403-07 (2012); Kim et al., *Biomaterials*, 33, 3959-66 (2012); Gonzalez-Toro et al., Journal of American Chemical Society, 134, 6964-67 (2012); and Slowing et al., Journal of American Chemical Society, 129, 8845-49 (2007). Generally, they are obtained by incubating a lipid-like compound and a pharmaceutical agent in a buffer such as a sodium acetate buffer or a phosphate buffer. The nanocomplexes thus obtained have a particle size of 50 to 1000 nm (e.g., 50 to 500 nm, 50 to 300 nm, and 50 to 180 nm).

Further, this invention covers a pharmaceutical composition containing the nanocomplex described above and a pharmaceutically acceptable carrier. The pharmaceutical carrier is compatible with the nanocomplex and should not be deleterious to the subject to be treated.

Moreover, another aspect of this invention relates to a method of administering an effective amount of the nanocomplex described above to a patient in need. "An effective amount" refers to the amount of the nanocomplex that is required to confer a therapeutic effect on the treated subject. Effective doses will vary, as recognized by those skilled in the art, depending on the types of diseases treated, route of administration, excipient usage, and the possibility of co-usage with other therapeutic treatment.

To practice the method of the present invention, a composition having the above-described nanocomplex can be administered parenterally, orally, nasally, rectally, topically, or buccally. The term "parenteral" as used herein refers to subcutaneous, intracutaneous, intravenous, intramuscular, intraarticular, intraarterial, intrasynovial, intrasternal, intrathecal, intralesional, or intracranial injection, as well as any suitable infusion technique.

A sterile injectable composition can be a solution or suspension in a non-toxic parenterally acceptable diluent or solvent, such as a solution in 1,3-butanediol. Among the acceptable vehicles and solvents that can be employed are mannitol, water, Ringer's solution, and isotonic sodium chloride solution. In addition, fixed oils are conventionally employed as a solvent or suspending medium (e.g., synthetic mono- or diglycerides). Fatty acid, such as oleic acid and its glyceride derivatives are useful in the preparation of injectables, as are natural pharmaceutically acceptable oils, such as olive oil or castor oil, especially in their polyoxyethylated versions. These oil solutions or suspensions can also contain a long chain alcohol diluent or dispersant, carboxymethyl cellulose, or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purpose of formulation.

A composition for oral administration can be any orally acceptable dosage form including capsules, tablets, emulsions and aqueous suspensions, dispersions, and solutions.

In the case of tablets, commonly used carriers include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A nasal aerosol or inhalation composition can be prepared according to techniques well known in the art of pharmaceutical formulation. For example, such a composition can be prepared as a solution in saline, employing benzyl alcohol or other suitable preservatives, absorption promoters to enhance bioavailability, fluorocarbons, and/or other solubilizing or dispersing agents known in the art.

A composition having the nanocomplexes can also be administered in the form of suppositories for rectal administration.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Preparation of Lipid-Like Compound EC16-63

Compound EC16-63 was prepared using N,N'-dimethyl-1,3-propanediamine and 1,2-epoxyhexadecane, as shown below:

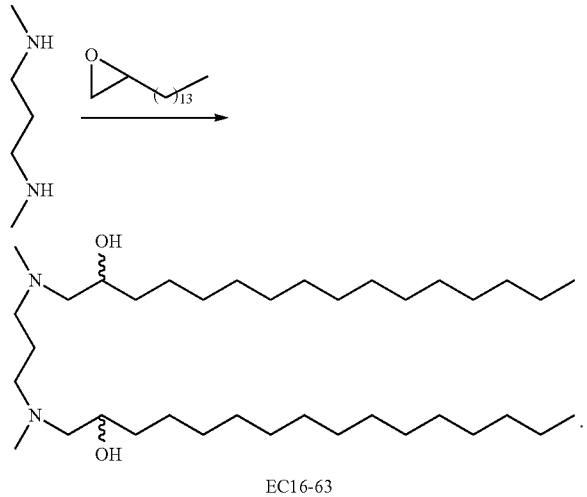

EC16-63

In a 5-mL Teflon-lined glass screw-top vial, 1,2-epoxyhexadecane was added to N,N'-dimethyl-1,3-propanediamine at a molar ratio of 2.4:1. The mixture was stirred at 80° C. for two days. After cooling, lipid-like compound EC16-63 thus formed was purified using flash chromatography on silica gel and characterized by proton nuclear magnetic resonance.

Protein Modification

Protein RNase A was modified using cis-aconitic anhydride following the procedures described below.

RNase A was dissolved in 0.1 M $NaHCO_3$ buffer solution (pH=9.5). After the resultant solution was cooled to 4° C., cis-aconitic anhydride was added in two batches, i.e., 50 mg and 10 mg. After stirring at room temperature for two hours, the reaction was complete to yield the aconitic acid modified RNase A (hereinafter "RNase A-Aco"), which was enriched by centrifugal filtration three times (Amicon Ultra, MWCO=10000, Millipore, Billerica, Mass.) and subsequent dialysis against $NaHCO_3$ buffer (25 mM, pH=9.5) for 24 hours.

Preparation of Composition A

Compound EC16-63 was dissolved in a phosphate buffer (25 mM, pH=7.4) at a concentration of 12 μg/mL. RNase A-Aco was added to the resultant mixture and incubated for 15 minutes at room temperature. The weight ratio between Compound EC16-63 and RNase A-Aco was 6:5.

Comparative Composition A' was also prepared following the same procedure described above except that RNase A was used instead of RNase A-Aco.

Both compositions were subjected to the in vitro assay described in Example 5 below. The results are also shown in that example.

Example 2

Composition B was prepared following the same procedure described in Example 1 above except that a light responsive RNase A was used instead of RNase A-Aco.

The light responsive RNase A was obtained following the same procedure also described in Example 1 except that carbonate

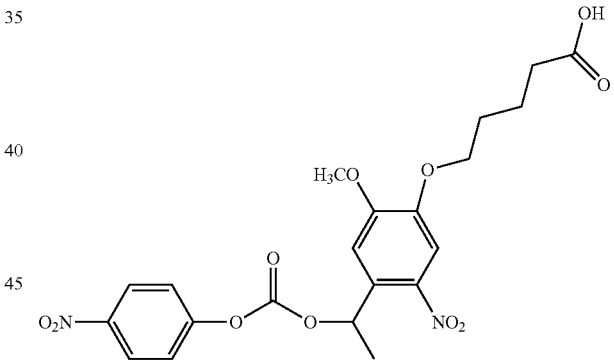

was used instead of cis-aconitic anhydride. See Scheme 3 above.

Comparative Composition B' was prepared following the same procedure used to prepare Composition B, except that no lipid-like compound was used.

Both compositions were subjected to the in vitro assay described in Example 5 below and the results are shown in FIG. 1 also below.

Example 3

Composition C was prepared using the same procedure described in Example 1 above except that a disulfide modified RNase A was used instead of RNase A-Aco.

The disulfide modified RNase A was obtained following the same procedure described also in Example 1 except that disulfide

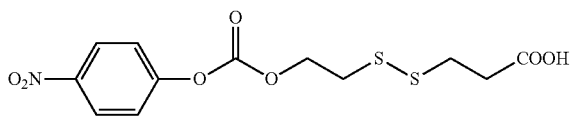 [SMILES: O=C(O)CCSSCCOC(=O)Oc1ccc([N+](=O)[O-])cc1]

was used instead of cis-aconitic anhydride. See Scheme 1 above.

Comparative Composition C' was prepared following the same procedure used to prepare Composition C, except that no lipid-like compound was used.

The two compositions were subjected to the in vitro assay described in Example 5 and the results are shown in FIG. 1.

Example 4

Composition D was prepared using the same procedure described in Example 1 above except that RNase A-BNC shown in Scheme 5 was used instead of RNase A-Aco.

RNase A-BNC was obtained following the same procedure described also in Example 1 except that boronic acid ester

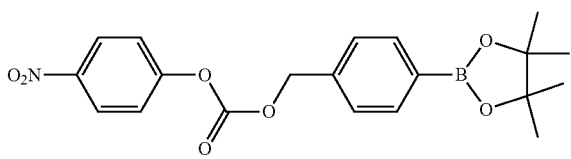 [SMILES: CC1(C)OB(c2ccc(COC(=O)Oc3ccc([N+](=O)[O-])cc3)cc2)OC1(C)C]

was used instead of cis-aconitic anhydride. See Scheme 5 above.

Comparative Composition D' was prepared following the same procedure used to prepare Composition D, except that RNase A-NC was used, which was prepared following the same procedure as RNase A-BNC except that

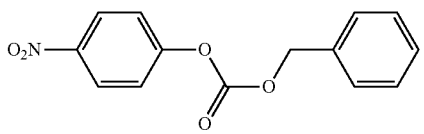

was used instead of the boronic acid ester.

Comparative Composition D" was prepared following the same procedure used to prepare Composition D, except that no lipid-like compound was used.

The three compositions were subjected to the in vitro assay described in Example 5.

Example 5

Compositions A-D and Comparative Compositions A'-D' and D" were tested for delivery of RNase A into B16F10 cancer cells.

Cell Culture

B16F10 cancer cells were cultured in Dulbecco's Modified Eagle Medium supplemented with 10% Fetal Bovine Serum and 1% penicillin/streptomycin at 37° C. in the presence of 5% $CO_2$. For the protein transfection assay described below, cells were seeded in 96-well plates at a density of 10,000 cells per well a day prior to transfection.

In Vitro Protein Transfection

To evaluate protein delivery efficiency, Compositions A-D and Comparative Compositions A'-D' and D" described in Examples 1-4 were added to B16F10 cancer cells and incubated at 37° C. for 24 hours. The protein concentration was 3.3 µg/mL in PBS. Compound EC16-63, dissolved in the same volume of PBS, was used as a control. The cell viability was determined by the Alamar Blue assay after 24 hours of incubation. All transfection studies were performed in quadruplicate.

For cells treated with Composition A, their viability was 45%; and for cells treated with Comparative Composition A', their viability was 100%. Note that low viability is an indication of high delivery efficiency. Unexpectedly, Composition A demonstrated high delivery efficiency, while Comparative Composition A' was not delivered.

For cells treated with Composition B, their viability was 50%; for cells treated with Comparative Composition B', their viability was 95%; for cells treated with Composition C, their viability was 20%; for cells treated with Comparative Composition C', their viability was 85%; and for cells treated with Compound EC16-63, their viability was 90%. Unexpectedly, Compositions B and C demonstrated much higher delivery efficiency than their corresponding Comparative Compositions B' and C'. As expected, Compound EC16-63 showed low cytotoxicity.

For cells treated with Composition D (dosage at 4 µg/mL), their viability was 30%; for cells treated with Comparative Composition D' (dosage at 4 µg/mL), their viability was 70%; and for cells treated with Comparative Composition D" (dosage at 4 µg/mL), their viability was 95%. Unexpectedly, Composition D showed much higher delivery efficiency than their corresponding Comparative Compositions D' and D".

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A nanocomplex comprising a delivery agent and a pharmaceutical agent, wherein the nanocomplex has a particle size of 50 to 1000 nm, the delivery agent binds to the pharmaceutical agent via non-covalent interaction or covalent bonding, and the pharmaceutical agent is a modified peptide or protein, comprising a peptide or protein and an added chemical moiety, wherein the added chemical moiety comprises a reactive oxygen species responsive group, wherein the reactive oxygen species responsive group comprises a boronic ester group; and the added chemical moiety is:

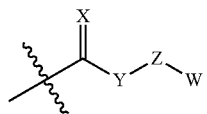

wherein:

W is the boronic ester group;

X is O, S, or $NR_e$, wherein $R_e$, is H, OH, an amino acid radical, a peptide radical, a $C_1$-$C_{10}$ monovalent aliphatic radical, a $C_1$-$C_{10}$ monovalent heteroaliphatic radical, a monovalent aryl radical, or a monovalent heteroaryl radical;

Y is a bond, O, S, or $NR_f$, wherein $R_f$ is H, OH, an amino acid radical, a peptide radical, a $C_1$-$C_{10}$ monovalent aliphatic radical, a $C_1$-$C_{10}$ monovalent heteroaliphatic radical, a monovalent aryl radical, or a monovalent heteroaryl radical; and Z is $R_h$-$A_7$-$A_8$-$R_i$, wherein $R_h$ and $R_i$, independently, are a bond or a $C_1$ aliphatic radical; $A_7$ is a bivalent aryl radical or a bivalent heteroaryl radical; and $A_8$ is a bond; and the delivery agent is a surfactant, a lipid, a lipid-like compound, a polymer, a dendrimer, an inorganic nanoparticle, a polymer nanoparticle, an inorganic nanowire, a polymer nanowire, a nanotube, or a combination thereof; wherein the lipid-like compound has the following formula:

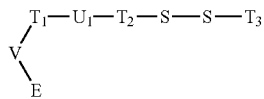

wherein:

V is a hydrophilic head:

E is a $C_1$-$C_{24}$ monovalent aliphatic radical, a $C_1$-$C_{24}$ monovalent heteroaliphatic radical, a monovalent aryl radical, a monovalent heteroaryl radical, or $T_4$-$U_2$-$T_5$-S—S-$T_6$; $T_2$-S—S-$T_3$ is a hydrophobic tail; and $U_1$ and $U_2$ are each a linker, wherein each of $T_1$ and $T_4$, independently, is a bond, a $C_1$-$C_{10}$ bivalent aliphatic radical, a $C_1$-$C_{10}$ bivalent heteroaliphatic radical, a bivalent aryl radical, or a bivalent heteroaryl radical; each of $T_2$ and $T_5$, independently, is a bond, a $C_1$-$C_{20}$ bivalent aliphatic radical, a $C_1$-$C_{20}$ bivalent heteroaliphatic radical, a bivalent aryl radical, or a bivalent heteroaryl radical; each of $T_3$ and $T_6$, independently, is a $C_1$-$C_{20}$ monovalent aliphatic radical, a $C_1$-$C_{20}$ monovalent heteroaliphatic radical, a monovalent aryl radical, or a monovalent heteroaryl radical; and S—S stands for a disulfide moiety.

2. The nanocomplex of claim 1, wherein the added chemical moiety is linked to the peptide or protein via an amide group, an ester group, an amidine group, a urea group, a carbamate group, an imidoester group, or a carbonate group.

3. The nanocomplex of claim 2, wherein the added chemical moiety is linked to the peptide or protein via an amide group, an ester group, or a carbamate group.

4. The nanocomplex of claim 1, wherein the added chemical moiety is:

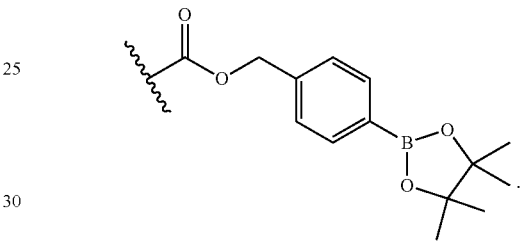

5. The nanocomplex of claim 1, wherein the delivery agent is a surfactant, a lipid, a lipid-like compound, a polymer, or a combination thereof.

* * * * *